US009267912B2

United States Patent
Maeda

(10) Patent No.: US 9,267,912 B2
(45) Date of Patent: Feb. 23, 2016

(54) APPARATUS FOR ANALYZING GAS INFORMATION

(75) Inventor: Seiji Maeda, Inazawa (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 135 days.

(21) Appl. No.: 13/323,015

(22) Filed: Dec. 12, 2011

(65) Prior Publication Data

US 2012/0160008 A1     Jun. 28, 2012

(30) Foreign Application Priority Data

Dec. 16, 2010   (JP) .................................. 2010-280682

(51) Int. Cl.
G01M 15/10    (2006.01)
G01N 27/406   (2006.01)

(52) U.S. Cl.
CPC .................................. G01N 27/4067 (2013.01)

(58) Field of Classification Search
CPC ... G01N 29/326; G01M 15/10; G01M 15/102
USPC ........................................................ 73/23.31
See application file for complete search history.

(56) References Cited

U.S. PATENT DOCUMENTS

2005/0132795 A1*   6/2005  Kobayashi et al. ........ 73/204.15
2007/0010932 A1    1/2007  Gotoh et al.

FOREIGN PATENT DOCUMENTS

JP         7-269401 A    10/1995
JP        2007-17154 A    1/2007

* cited by examiner

Primary Examiner — Laura Martin
Assistant Examiner — Alex Devito
(74) Attorney, Agent, or Firm — Sughrue Mion, PLLC

(57) ABSTRACT

A gas information estimation apparatus (100) is connected to a gas sensor element for detecting the concentration of gas flowing through an internal combustion engine (11), and estimates gas information other than the concentration. The apparatus includes gas sensor element provisional temperature calculation means (51) for calculating a provisional temperature of the gas sensor element using a predetermined simulation model, and inputting a reference value to the model as the parameter value; gas sensor element actual temperature measurement means (53), (54); gas information calculation means (55) for calculating the true value of the parameter value which can be input to the model in place of the reference value such that the provisional temperature of the gas sensor element approaches the actual temperature; and gas information obtaining means (57) for obtaining an estimative value of the gas information from the true value.

3 Claims, 2 Drawing Sheets

APPARATUS FOR ANALYZING GAS INFORMATION

TECHNICAL FIELD

The present invention relates to a gas information estimation apparatus that estimates gas information regarding a flow gas flowing through an internal combustion engine (intake gas flowing through the intake pipe thereof or exhaust gas flowing through the exhaust pipe thereof).

BACKGROUND ART

Conventionally, there has been developed an apparatus for controlling the air-fuel ratio of an internal combustion engine, which apparatus estimates the temperature of a detection element of an air-fuel ratio sensor provided in the exhaust system of the engine, and corrects air-fuel ratio control when the detection element has not yet reached its activation temperature, to thereby reduce fluctuation of the air-fuel ratio (Patent Document 1). Also, there has been developed a technique of estimating the temperature of a gas sensor element provided in the exhaust system of an internal combustion engine through use of a predetermined model, and comparing it with an element temperature calculated from the impedance of the gas sensor element so as to determine the degree of deterioration of the sensor (Patent Document 2).

The above-described estimation of the temperature of the gas sensor element is performed as follows, for example. First, there is prepared a relational expression which represents the relation between the heat reception and radiation amounts of the gas sensor element and exhaust gas temperature, etc. Also, there is prepared a model which represents the relation between the heat reception and radiation amounts and the temperature of the gas sensor element. The heat reception and radiation amounts of the gas sensor element are calculated on the basis of a measurement value provided by a measurement sensor (a temperature sensor or a flow velocity sensor) attached to the exhaust system of the internal combustion engine, and the temperature of the gas sensor element is estimated by the above-described model (an element temperature estimation model).

PRIOR ART DOCUMENTS

Patent Documents

[Patent Document 1] Japanese Patent Application Laid-Open (kokai) No. H7-269401
[Patent Document 2] Japanese Patent Application Laid-Open (kokai) No. 2007-17154

SUMMARY OF THE INVENTION

Problems to be Solved by the Invention

The above-described measurement sensor (a temperature sensor or a flow velocity sensor) is also required to monitor the activation state of an exhaust gas purification catalyst unit attached to an internal combustion engine and/or to protect an exhaust turbine. However, since such a measurement sensor is relatively expensive, employment of such a measurement sensor raises a problem of increasing the total cost of the control system of the internal combustion engine. Also, when the number of measurement sensors increases, the number of sensors which fail or deteriorate increases accordingly, whereby the stability of the control system may drop.

In view of the above-described problems, an object of the present invention is to provide a gas information estimation apparatus which can estimate gas information (e.g., temperature) other than concentration of a flow gas which flows through an internal combustion engine, by making use of a gas sensor element for detecting the concentration of a specific gas component of the flow gas, to thereby eliminate the necessity of a measurement sensor for measuring the gas information to be estimated.

Means for Solving the Problems

In order to solve the above-described problems, the present invention provides a gas information estimation apparatus which is connected to a gas sensor element for detecting the concentration of a specific gas component of a flow gas flowing through an internal combustion engine and which estimates gas information regarding the flow gas other than the concentration. The gas information estimation apparatus comprises gas sensor element provisional temperature calculation means for calculating a provisional temperature of the gas sensor element by using a predetermined simulation model which can provide an estimated temperature of the gas sensor element on the basis of at least a parameter value regarding the gas information to be estimated, and inputting a reference value to the model as the parameter value; gas sensor element actual temperature measurement means for measuring the actual temperature of the gas sensor element; gas information calculation means for calculating a true value of the parameter value which can be input to the model in place of the reference value such that the provisional temperature calculated by the gas sensor element provisional temperature calculation means falls within a predetermined range centered on the actual temperature measured by the gas sensor element actual temperature measurement means; and gas information obtaining means for obtaining an estimative value of the gas information on the basis of the true value calculated by the gas information calculation means.

According to such a gas information estimation apparatus, the true value of the parameter value regarding the gas information which is calculated by the gas information calculation means such that the provisional temperature calculated by the gas sensor element provisional temperature calculation means falls within a predetermined range centered on the actual temperature of the gas sensor element (actually measured temperature) and which can be input to the model in place of the reference value is considered to approximate the true value of the gas information. That is, through use of a simulation model which can provide the estimated temperature of the gas sensor element on the basis of the parameter value regarding the gas information and through measurement of the actual temperature of the gas sensor element, reverse calculation of the model becomes possible, and the parameter value of the gas information input to the model can be calculated. As a result, estimation of the gas information becomes possible. Since accurate estimation of the gas information can be realized, a measurement sensor for actually measuring the gas information becomes unnecessary, and the total cost of the control system of the internal combustion engine can be reduced. In addition, since the number of measurement sensors decreases, the stability of the system is improved. Notably, from the viewpoint of improving the estimation accuracy of the gas information, desirably, the "predetermined range" of the present invention is set to as narrow a range as possible; for example, a range of ±10° C. (preferably, a range of ±5° C.)

In the case where the gas information is at least one of the temperature, flow velocity, and pressure of exhaust gas of the internal combustion engine, since measurement sensors for measuring these parameters are relatively expensive, the total cost of the control system of the internal combustion engine can be lowered further.

In the gas information estimation apparatus of the present invention, the gas sensor element actual temperature measurement means may detect the impedance of the gas sensor element, and measure the actual temperature from the impedance.

Since the impedance of the gas sensor element changes with the temperature thereof, the actual temperature of the gas sensor element can be measured accurately through detection of the impedance, whereby the gas information can be estimated accurately.

Effect of the Invention

According to the present invention, it is possible to accurately estimate the gas information, other than concentration, of a flow gas which flows through an internal combustion engine, by making use of a gas sensor element for detecting the concentration of a specific gas component of the flow gas, to thereby eliminate the necessity of a measurement sensor for measuring the gas information.

MODE FOR CARRYING OUT THE INVENTION

An embodiment of the present invention will now be described.

Figure 1:
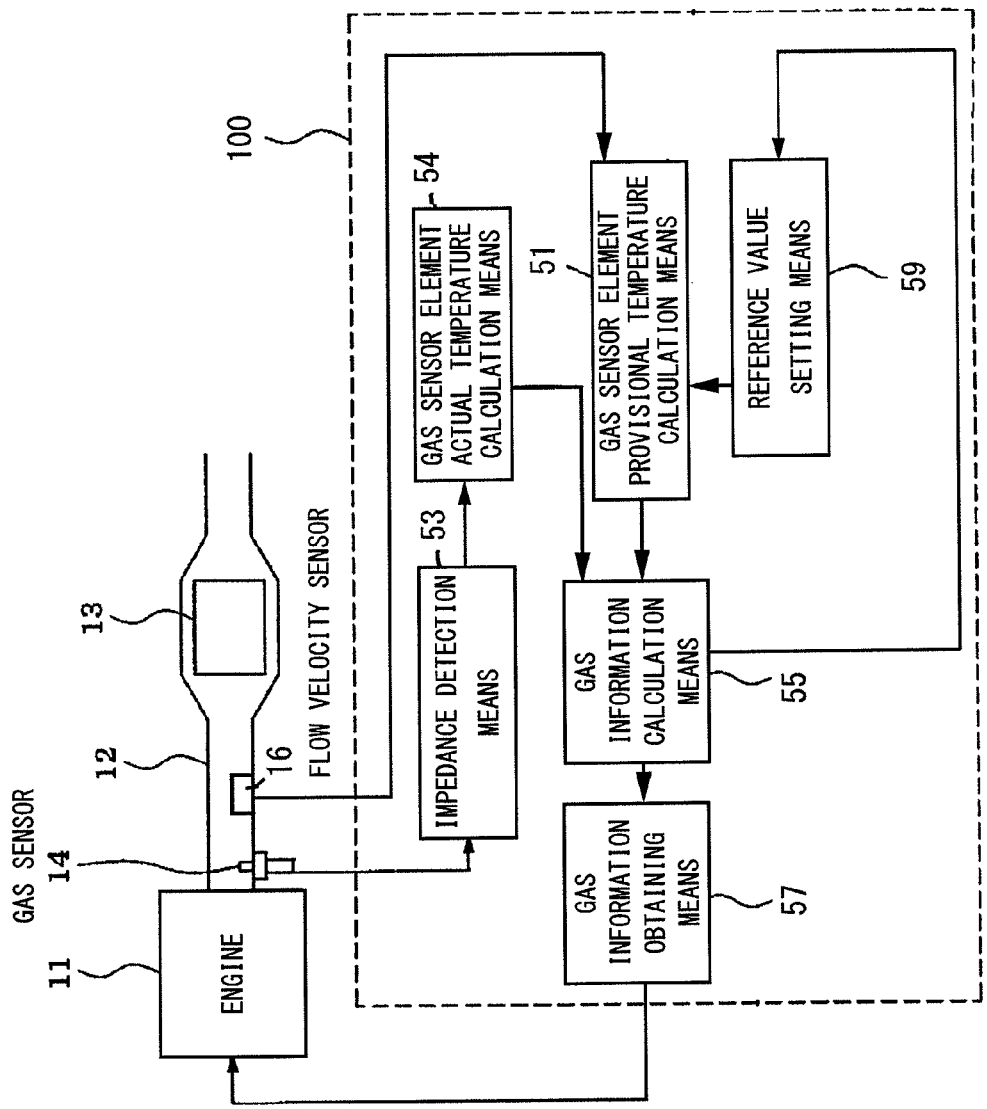
FIG. 1 Block diagram of a gas information estimation apparatus according to an embodiment of the present invention.

FIG. 1 is a block diagram of a gas information estimation apparatus 100 according to the embodiment of the present invention.

A three-way catalyst 13 for reducing CO, HC, $NO_x$, etc. contained in exhaust gas (corresponding to "flow gas" in the claims) is provided in an exhaust pipe 12 of an internal combustion engine 11, and a gas sensor 14 for detecting the oxygen concentration of exhaust gas is provided on the upstream side of the catalyst 13. A gas sensor element (not shown) of the gas sensor 14 includes, for example, at least one cell composed of an oxygen-ion-conductive zirconia solid electrolyte member and a pair of electrodes formed on the surface of the member, and the oxygen concentration can be calculated from the output of the cell. Also, a heater is provided on the gas sensor element so as to quickly activate the gas sensor element.

Furthermore, a flow velocity sensor 16 for measuring the flow velocity of exhaust gas is attached to the exhaust pipe 12. The output of the flow velocity sensor 16 (a value representing the flow velocity of exhaust gas) is used for calculation of a provisional temperature of the sensor element performed through use of a model which will be described later, and for control of the engine 11.

The gas information estimation apparatus 100 reads the output of the gas sensor 14 while the engine is operating, and feedback-controls the amount of fuel injection such that the air-fuel ratio of exhaust gas coincides with a target air-fuel ratio, and controls the engine 11 on the basis of the output of the flow velocity sensor 16 and the estimated exhaust gas temperature to be described later.

Also, the gas information estimation apparatus 100 includes gas sensor element provisional temperature calculation means 51 for calculating a provisional temperature of the gas sensor element through use of a predetermined simulation model (a calculation expression or a map) which can provide an estimated temperature of the gas sensor element, and on the basis of the output of the flow velocity sensor 16 and a reference value serving as a parameter value regarding the temperature of exhaust gas (corresponding to "gas information" in the claims) to be estimated; impedance detection means 53 for detecting the impedance of the gas sensor element; gas sensor element actual temperature calculation means 54 for calculating the actual temperature of the gas sensor element from the impedance detected by the impedance detection means 53; gas information calculation means 55 for calculating the true value of the parameter value which can be input to the model in place of the reference value such that the provisional temperature calculated by the gas sensor element provisional temperature calculation means 51 falls within a predetermined range (in the present embodiment, a range of ±5° C.) centered on the actual temperature calculated by the gas sensor element actual temperature calculation means 54 (actually measured temperature); gas information obtaining means 57 for obtaining an estimative value of the gas information from the true value calculated by the gas information calculation means; and reference value setting means 59 for storing as an updated reference value, the true value of the parameter value calculated by the gas information calculation means 55. Notably, the impedance detection means 53 and the gas sensor element actual temperature calculation means 54 correspond to "gas sensor element actual temperature measurement means" in the claims.

Notably, the gas information estimation apparatus 100 is an electronic control unit (ECU) composed of a microcomputer including a CPU (central processing unit), RAM, ROM, etc.; and a predetermined analog circuit. Various types of processing to be described later are performed by the CPU through execution of computer programs stored in the ROM.

Specifically, the impedance detection means 53 is realized by an analog circuit; and the gas sensor element provisional temperature calculation means 51, the gas sensor element actual temperature calculation means 54, the gas information calculation means 55, and the gas information obtaining means 57 are realized by the CPU that executes the computer programs stored in the ROM. The reference value setting means 59 is realized by a storage medium provided separately from the microcomputer.

The gas sensor element provisional temperature calculation means 51 estimates the temperature of the gas sensor element through use of the predetermined model and on the basis of the temperature of exhaust gas and the flow velocity of exhaust gas, which is the output of the flow velocity sensor 16. This calculation model can be formed by a calculation expression, a map, or the like. For example, the model can be created as follows. There is prepared a relational expression which represents the relation between the heat reception and radiation amounts of the gas sensor element, and the temperature and flow velocity of exhaust gas. Also, there is prepared a relational expression which represents the relation between the heat reception and radiation amounts and the temperature of the gas sensor element. Thus, the above-mentioned model is prepared.

As described in Patent Document 2, the above-mentioned model can be represented by the following calculation expression.

$$cM \cdot dTu/dt = [\text{heat received from exhaust gas}] - [\text{heat radiated to outside air}] + [\text{heat generated by the heater}] = A \cdot Re^m \cdot (Te-Tu) - B(Tu-Ta) + I^2 \cdot R$$

In the calculation expression, cM is the thermal capacity of the gas sensor element, and dTu/dt is the time-differentiated value of the element temperature Tu.

Also, the heat received from exhaust gas, the heat radiated to outside air, and the heat generated by the heater are represented by the following expressions.

Heat received from exhaust gas = $A \cdot Re^m \cdot (Te-Tu)$

A: the coefficient of heat transfer of exhaust gas
Te: the temperature of exhaust gas
Tu: the temperature of the gas sensor element (that is, the provisional temperature of the gas sensor element)
Re: Reynolds number
m: power (index)

Heat radiated to outside air = $-B(Tu-Ta)$

B: the coefficient of heat transfer of outside air
Tu: the temperature of the gas sensor element (that is, the provisional temperature of the gas sensor element)
Ta: the temperature of outside air Heat generated by the heater = $I^2 \cdot R$ I: heater current
R: heater resistance Notably, the flow velocity of exhaust gas, which is the output of the flow velocity sensor 16, is used for setting the value of Re (Reynolds number). Also, Ta (the temperature of outside air) is measured by an unillustrated temperature sensor. In the present embodiment, of the various values input to the model, the temperature of exhaust gas is unknown. Therefore, in the present embodiment, the gas sensor element provisional temperature (Tu) is calculated through use of the above-described model and a reference value of the exhaust gas temperature stored in the reference value setting means 59.

Notably, the gas sensor element provisional temperature calculation means 51 is configured such that every time the provisional temperature is calculated, the latest reference value stored in the reference value setting means 59 is input to the model. An initial value is set in the reference value setting means 59. When the gas information estimation apparatus 100 is started, this initial value is used as the first reference value. After that, every time the gas information calculation means 55 calculates a new true value of the parameter value, the true value is stored in the reference value setting means 59 as the updated or latest reference value.

The impedance detection means 53 and the gas sensor element actual temperature calculation means 54 have a function of detecting the impedance of the gas sensor element. Since the impedance of the gas sensor element depends on the temperature of the gas sensor element, the actual temperature of the gas sensor element can be measured.

Notably, the impedance detection means 53 has a known configuration for supplying a predetermined pulse voltage or pulse current to the gas sensor element (cell), and detecting a change in the output of the gas sensor element at that time. The gas sensor element actual temperature calculation means 54 is configured to calculate the impedance of the gas sensor element on the basis of the change in the output of the gas sensor element and the predetermined pulse voltage or pulse current supplied to the gas sensor element, and calculate the actual temperature (actually measured temperature) of the gas sensor element on the basis of the relation (e.g., a map) between the impedance and the temperature of the gas sensor element.

The gas information calculation means 55 calculates, through use of a calculation expression for PI control or PID control, the true value of the parameter value of the exhaust gas temperature which can be input to the model in place of the reference value input from the reference value setting means 59, such that the provisional temperature of the gas sensor element calculated by the gas sensor element provisional temperature calculation means 51 falls within a predetermined range (in the present embodiment, a range of ±5° C.) centered on the actual temperature of the gas sensor element calculated by the gas sensor element actual temperature calculation means 54 (actually measured temperature).

Subsequently, the gas information obtaining means 57 finally obtains an estimative value of the exhaust gas temperature to be estimated, from the true value of the parameter value of the exhaust gas temperature calculated by the gas information calculation means 55. The exhaust gas temperature calculated by the gas information calculation means 55 such that the provisional temperature calculated by the gas sensor element provisional temperature calculation means 51 falls within the predetermined range centered on the actually measured temperature is considered to approximate the true value of the exhaust gas temperature. That is, by means of estimating one piece of the gas information input to the gas sensor element provisional temperature calculation means 51, a measurement sensor for actually measuring that gas information becomes unnecessary. Thus, the total cost of the control system of the internal combustion engine can be reduced. In addition, since the number of measurement sensors decreases, the stability of the system is improved. That is, the true value of the parameter value—which is calculated by the gas information calculation means 55 such that the provisional temperature calculated by the gas sensor element provisional temperature calculation means 51 falls within a predetermined range centered on the actually measured temperature of the gas sensor element and which is input to the model in place of the reference value—is considered to approximate the true value of the exhaust gas temperature. That is, through use of a simulation model which can provide the estimated temperature of the gas sensor element on the basis of at least the exhaust gas temperature and through measurement of the actual temperature of the gas sensor element, reverse calculation of the model becomes possible, and the parameter value of the exhaust gas temperature (Te) input to the model can be calculated. As a result, estimation of the gas information becomes possible.

Notably, in the present embodiment, the gas information which is input to the model in the gas sensor element provisional temperature calculation means 51 and which is to be estimated is the exhaust gas temperature. However, the gas information to be estimated is not limited to the exhaust gas temperature. If selected gas information of exhaust gas of the internal combustion engine is a parameter value used for the simulation model which can provide the estimated temperature of the gas sensor element, under the concept of the present invention, the gas information can be estimated without providing a measurement sensor for measuring the gas information to be estimated. Notably, specific examples of gas information which replace the exhaust gas temperature used in the present embodiment include the flow velocity and pressure of exhaust gas of the internal combustion engine.

Figure 2:
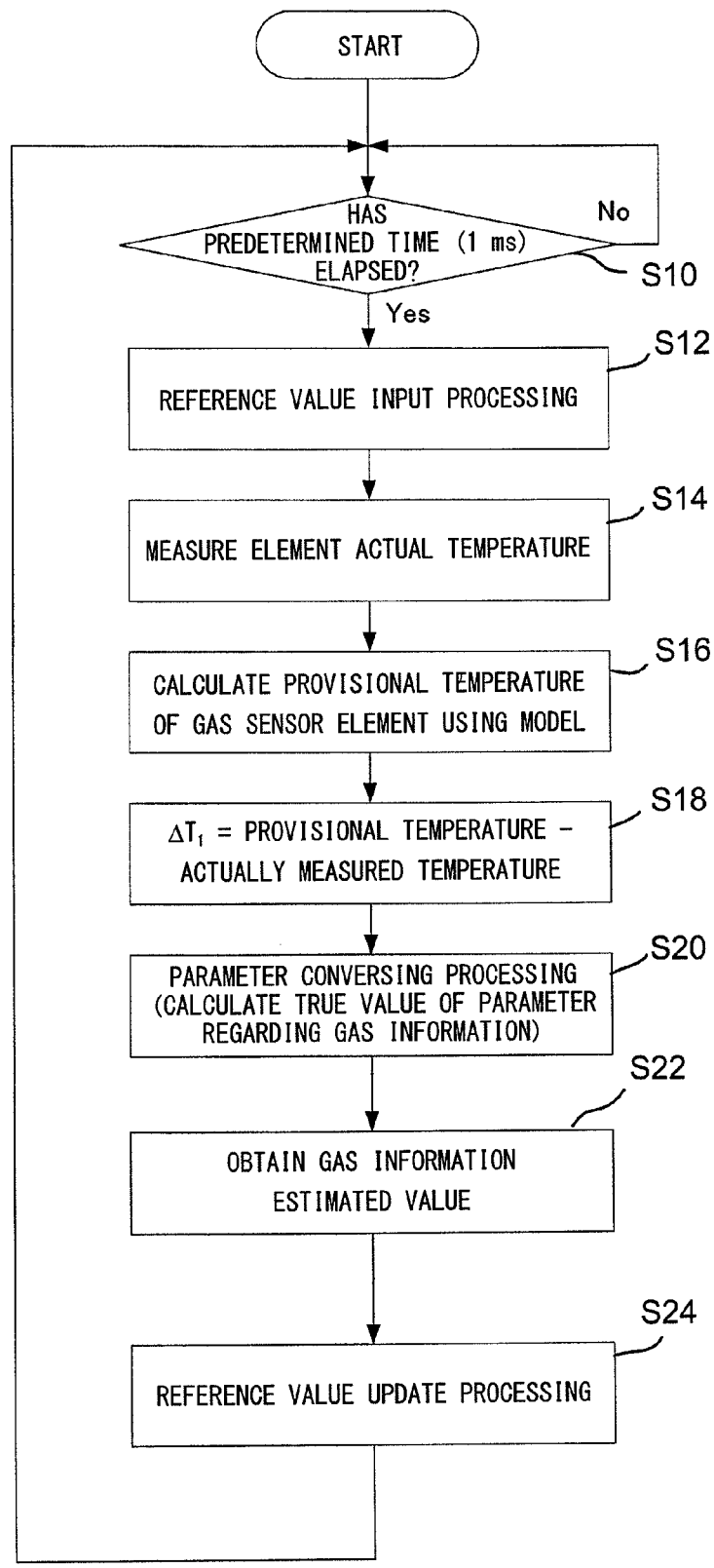
FIG. 2 Flowchart showing processing performed by the gas information estimation apparatus.

FIG. 2 is a flowchart showing processing performed by the gas information estimation apparatus 100 of the present embodiment. First, the gas information estimation apparatus 100 waits until a predetermined period of time (e.g., 1 ms) elapses (until the timing of starting the processing has come) (step S10). In the case where the predetermined period of time has elapsed ("Yes" in step S10), the gas information estimation apparatus 100 proceeds to step S12, and performs processing of obtaining (reading) the latest reference value from the reference value setting means 59 (step S12). Notably, as described above, the reference value set in the reference value setting means 59 is updated periodically. However, at the first reading operation after the startup, the gas information estimation apparatus 100 reads the previously set initial value as the reference value. Meanwhile, in the case where the predetermined period of time has not yet elapsed ("No" in step S10), the gas information estimation apparatus 100 repeats the processing of step S10 until the predetermined period of time elapses.

After completion of the processing of step S12, the gas sensor element actual temperature calculation means 54 calculates the impedance of the gas sensor element on the basis of the output from the impedance detection means 53, and measures the actual temperature of the gas sensor element (step S14). Subsequent to step S14, the gas sensor element provisional temperature calculation means 51 calculates the provisional temperature (Tu) of the gas sensor element in accordance with the above-described model (calculation expression) by inputting the reference value of the exhaust gas temperature obtained in step S12 and the output of the flow velocity sensor 16 to the model (step S16). The calculation in accordance with the model is performed on the basis of information regarding the outside air temperature, and information regarding the heating by the heater (heater current, heater resistance).

Subsequent to step S16, the gas information calculation means 55 calculates the difference $\Delta T_1$ between the provisional temperature of the gas sensor element calculated in step S16 and the actual temperature of the gas sensor element measured in step S12 (step S18), and performs parameter converging processing (computation through use of a calculation expression for PI control or PID control) for calculating the true value of the parameter representing the exhaust gas temperature which can be input to the model in place of the reference value such that $\Delta T_1$ falls within the predetermined range (step S20).

Next, the gas information estimation apparatus 100 proceeds to step 22, and obtains an estimative value of the exhaust gas temperature to be estimated, from the true value of the parameter representing the exhaust gas temperature calculated in step S20. The estimative value of the exhaust gas temperature obtained in S22 is used for various types of control of the engine, together with the output value regarding the oxygen concentration obtained from the gas sensor 14. After completion of the processing of step S22, the gas information estimation apparatus 100 performs processing of updating the reference value stored in the reference value setting means 59 such that the true value of the parameter (representing the exhaust gas temperature) calculated in step S20 is stored as the latest reference value (step S24), and then returns to step S10. In this manner, the gas information estimation apparatus 100 can estimate the estimative value of the exhaust gas temperature without use of a measurement sensor for measuring the exhaust gas temperature.

Needless to say, the present invention is not limited to the above-described embodiment, and encompasses various modifications and equivalents which fall within the scope of the present invention.

For example, in the above-described embodiment, the gas sensor element provisional temperature calculation means 51 calculates the provisional temperature of the gas sensor element on the basis of two parameters; i.e., the reference value of the exhaust gas temperature and the output of the flow velocity sensor 16. However, the number and types of the parameters may be changed in accordance with an employed model (a calculation expression or a map). For example, in addition to the above-mentioned two parameters, vehicle speed may be used.

In the above-described embodiment, the gas information estimation apparatus 100 of the present embodiment is built in the ECU. However, the gas information estimation apparatus may be provided separately from the ECU. A separate gas information estimation apparatus in which an analog circuit and a microcomputer capable of executing the above-described various types of processing are mounted on a circuit board may be provided between the gas sensor 14 and the ECU. In the above-described embodiment, the information (specifically, temperature) of exhaust gas of the engine 11 is the gas information to be estimated. However, the embodiment may be modified such that a gas sensor is attached to an intake pipe through which intake gas taken into the engine 11 flows, and an estimation value of information regarding intake gas flowing through the intake pipe (e.g., any of the temperature, flow velocity, and pressure of intake gas) is calculated.

DESCRIPTION OF REFERENCE NUMERALS

11: internal combustion engine (engine)
14: gas sensor
51: gas sensor element provisional temperature calculation means
53: impedance detection means (gas sensor element actual temperature measurement means)
54: gas sensor element actual temperature calculation means (gas sensor element actual temperature measurement means)
55: gas information calculation means
57: gas information obtaining means
100: gas information estimation apparatus

The invention claimed is:
1. A gas information system for an internal combustion engine, comprising:
   a gas information estimation apparatus; and
   a gas sensor element for detecting the concentration of a specific gas component of a flow gas flowing through the internal combustion engine,
   wherein the gas information estimation apparatus is connected to the gas sensor element and is configured to estimate information regarding the flow gas other than the concentration,
   the gas information estimation apparatus comprising:
   gas sensor element provisional temperature calculation means for calculating a provisional temperature of the gas sensor element by using a predetermined simulation model to provide an estimated temperature of the gas sensor element on the basis of at least a parameter value regarding the gas information to be estimated, and inputting a reference value to the model as the parameter value;
   gas sensor element actual temperature measurement means for measuring the actual temperature of the gas sensor element;
   gas information calculation means for calculating a true value of the parameter value to be input to the model in place of the reference value such that the provisional temperature calculated by the gas sensor element provisional temperature calculation means falls within a pre- determined range centered on the actual temperature measured by the gas sensor element actual temperature measurement means; and gas information obtaining means for obtaining an estimative value of the gas information on the basis of the true value calculated by the gas information calculation means.

2. A gas information system according to claim 1, wherein the gas information is at least one of the temperature, flow velocity, and pressure of exhaust gas of the internal combustion engine.

3. A gas information system according to claim 1, wherein the gas sensor element actual temperature measurement means detects the impedance of the gas sensor element, and measures the actual temperature from the impedance.

\* \* \* \* \*